United States Patent
Lee et al.

(10) Patent No.: US 10,213,131 B2
(45) Date of Patent: Feb. 26, 2019

(54) METHOD OF GENERATING MAGNETIC RESONANCE IMAGE AND MEDICAL IMAGING APPARATUS USING THE METHOD

(71) Applicant: SAMSUNG ELECTRONICS CO., LTD., Suwon-si (KR)

(72) Inventors: Hoonjae Lee, Seoul (KR); Jin-young Hwang, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 522 days.

(21) Appl. No.: 14/918,741

(22) Filed: Oct. 21, 2015

(65) Prior Publication Data

US 2016/0109548 A1  Apr. 21, 2016

(30) Foreign Application Priority Data

Oct. 21, 2014  (KR) .................. 10-2014-0142781

(51) Int. Cl.
| | | |
|---|---|---|
| *A61B 5/055* | (2006.01) | |
| *G01R 33/561* | (2006.01) | |
| *G01R 33/563* | (2006.01) | |

(52) U.S. Cl.
CPC .......... *A61B 5/055* (2013.01); *G01R 33/5613* (2013.01); *G01R 33/56341* (2013.01)

(58) Field of Classification Search
CPC ............... A61B 5/055; G01R 33/5613; G01R 33/56341
(Continued)

(56) References Cited

U.S. PATENT DOCUMENTS 4,960,106 A * 10/1990 Kubokawa ........... A61B 1/0008
                                                      600/104
5,271,400 A * 12/1993 Dumoulin ............. A61B 5/055
                                                      128/899
(Continued)

FOREIGN PATENT DOCUMENTS

| CN | 102727206 A | 10/2012 |
|---|---|---|
| JP | 838433 A | 2/1996 |

(Continued)

OTHER PUBLICATIONS

Communication dated Jan. 5, 2016 issued by Korean Intellectual Property Office in counterpart Korean Application No. 10-2014-0142781.

(Continued)

*Primary Examiner* — Giovanni Astacio-Oquendo
(74) *Attorney, Agent, or Firm* — Sughrue Mion, PLLC

(57) ABSTRACT

A method of generating a medical resonance image and a medical imaging apparatus using the same are provided. The medical imaging apparatus includes a signal controller configured to determine flip angles respectively corresponding to radio frequency (RF) refocusing pulses included in a fast spin-echo (FSE) pulse sequence, based on a pseudo-steady state model of a flip angle schedule. The medical imaging apparatus further includes an RF transmitter configured to apply an RF excitation pulse to an object, and apply the RF refocusing pulses to the object based on the determined flip angles. The medical imaging apparatus further includes an image processor configured to generate a magnetic resonance (MR) image based on an MR signal that is received from the object.

20 Claims, 9 Drawing Sheets

(58) Field of Classification Search
USPC .................................... 324/300, 307, 309
See application file for complete search history.

(56) References Cited

U.S. PATENT DOCUMENTS

| | | | |
|---|---|---|---|
| 7,082,326 | B2 | 7/2006 | Johansson |
| RE40,587 | E * | 11/2008 | McKinnon ............. A61B 5/055 600/410 |
| 9,097,778 | B2 | 8/2015 | Bito et al. |
| 2007/0038077 | A1 | 2/2007 | Wiethoif et al. |
| 2008/0319301 | A1 | 12/2008 | Busse |
| 2016/0178714 | A1* | 6/2016 | Fautz ................... G01R 33/483 324/309 |
| 2017/0319097 | A1* | 11/2017 | Amthor ................. A61B 5/055 |
| 2018/0024214 | A1* | 1/2018 | Bhat ................. G01R 33/4828 324/309 |

FOREIGN PATENT DOCUMENTS

| | | |
|---|---|---|
| JP | 5189203 B2 | 4/2013 |
| KR | 10-0622772 B1 | 9/2006 |
| KR | 10-1056451 B1 | 8/2011 |

OTHER PUBLICATIONS

Communication dated May 11, 2016, issued by the Korean Intellectual Property Office in counterpart Korean Application No. 10-2014-0142781.

Jaeseok Park, et al., "Contrast-Enhanced, Three-Dimensional, Whole-Brain, Black-Blood Imaging: Application to Small Brain Metastases", Magnetic Resonance in Medicine 63, 2010, revised Aug. 30, 2009; accepted Sep. 30, 2009, pp. 553-561.

* cited by examiner 900-1

900-2

METHOD OF GENERATING MAGNETIC RESONANCE IMAGE AND MEDICAL IMAGING APPARATUS USING THE METHOD

CROSS-REFERENCE TO RELATED APPLICATION

This application claims priority from Korean Patent Application No. 10-2014-0142781, filed on Oct. 21, 2014, in the Korean Intellectual Property Office, the disclosure of which is incorporated herein in its entirety by reference.

BACKGROUND

1. Field

Methods and apparatus consistent with exemplary embodiments relate to methods and apparatuses for obtaining magnetic resonance (MR) images.

2. Description of the Related Art

Because a magnetic resonance imaging (MRI) apparatus, which is an apparatus for obtaining an image of an object by using a magnetic field three-dimensionally, is capable of showing a spine, a joint, a nervous system, and a ligament as well as a bone at an angle, the MRI apparatus is widely used to accurately diagnose a disease.

A medical imaging apparatus may obtain a magnetic resonance (MR) signal by using a contrast medium for enhancing a contrast between structures, may reconstruct the obtained MR signal, and may output the reconstructed signal. The contrast medium may enhance a signal obtained from target tissue that lacks a blood-brain barrier (BBB) or is in an incomplete state by increasing an intensity of the signal obtained from the target tissue. However, the contrast medium may also enhance a signal obtained from blood flow by increasing an intensity of the signal obtained from the blood flow.

Accordingly, there is a demand for a method of generating an image in which target tissue of an object is enhanced by using a contrast medium and a medical imaging apparatus using the method.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments include methods and apparatuses for calculating a variable flip angle of a fast spin-echo (FSE) pulse sequence and generating a magnetic resonance (MR) image by using the calculated variable flip angle.

One or more exemplary embodiments include methods and apparatuses for generating an image in which an intensity of a signal obtained from a tissue is selectively increased by suppressing an intensity of a signal obtained from blood flow based on an FSE pulse sequence.

According to an aspect of an exemplary embodiment, a medical imaging apparatus includes a medical imaging apparatus including a signal controller configured to determine flip angles respectively corresponding to radio frequency (RF) refocusing pulses included in a fast spin-echo (FSE) pulse sequence, based on a pseudo-steady state model of a flip angle schedule. The medical imaging apparatus further includes an RF transmitter configured to apply an RF excitation pulse to an object, and apply the RF refocusing pulses to the object based on the determined flip angles. The medical imaging apparatus further includes an image processor configured to generate a magnetic resonance (MR) image based on an MR signal that is received from the object.

The flip angle schedule may be determined based on a target tissue of the object.

The signal controller may be configured to determine a first echo train (ET) interval and a second ET interval based on a target tissue of the object, determine a first gradient corresponding to the first ET interval and a second gradient corresponding to the ET train interval, based on the pseudo-steady state model, and determine the flip angles respectively corresponding to the RF refocusing pulses, based on the first gradient and the second gradient.

The signal controller may be configured to determine flip angles corresponding to a start point and an end point of each of the first ET interval and the second ET interval, based on the flip angle schedule.

A flip angle corresponding to a first RF refocusing pulse, among the RF refocusing pulses, may be 180°.

The medical imaging apparatus may further include a gradient transmitter configured to apply a diffusion gradient magnetic field to the object before and after a first refocusing pulse, among the RF refocusing pulses, is applied, and a signal receiver configured to receive an MR signal from the object to which the diffusion gradient magnetic field is applied. The image processor may be configured to generate the MR image based on the received MR signal.

The diffusion gradient magnetic field may be generated in gradient magnetic fields in directions of X, Y, and Z axes.

The medical imaging apparatus may further include an output interface configured to divide the MR image into intervals according to an intensity of the MR signal, and display the intervals.

The medical imaging apparatus may further include an input interface configured to receive a user input, and the signal controller may be further configured to determine an echo train length of the FSE pulse sequence based on the user input.

According to an aspect of another exemplary embodiment, there is provided a method performed by a medical imaging apparatus to generate an image, the method including determining flip angles respectively corresponding to radio frequency (RF) refocusing pulses included in a fast spin-echo (FSE) pulse sequence, based on a pseudo-steady state model of a flip angle schedule. The method further includes applying an RF excitation pulse to an object, and applying the RF refocusing pulses to the object based on the determined flip angles. The method further includes generating a magnetic resonance (MR) image based on an MR signal that is received from the object.

The determining the flip angles may include determining a first echo train (ET) interval and a second ET interval based on a target tissue of the object, determining a first gradient corresponding to the first ET interval and a second gradient corresponding to the second ET interval, based on the pseudo-steady state model, and determining the flip angles respectively corresponding to the RF refocusing pulses, based on the first gradient and the second gradient.

The determining the first gradient and the second gradient may include determining flip angles corresponding to a start point and an end point of each of the first ET interval and the second ET interval, based on the flip angle schedule.

The method may further include applying a diffusion gradient magnetic field to the object before and after a first RF refocusing pulse, among the RF refocusing pulses, is applied, and receiving an MR signal from the object to which the diffusion gradient magnetic field is applied, and the generating may include generating the MR image based on the received MR signal.

The method may further include dividing the MR image into intervals according to an intensity of the MR signal, and displaying the intervals.

The method may further include receiving a user input, and determining an echo train length of the FSE pulse sequence based on the user input.

A non-transitory computer-readable storage medium may store a program comprising instructions configured to cause a computer to perform the method.

According to an aspect of another exemplary embodiment, a medical imaging apparatus includes a signal controller configured to determine flip angles respectively corresponding to radio frequency (RF) refocusing pulses, based on a flip angle schedule, and an RF transmitter configured to apply an RF excitation pulse to an object, and apply the RF refocusing pulses to the object based on the determined flip angles.

BRIEF DESCRIPTION OF THE DRAWINGS

The above and/or other aspects will become more apparent by describing exemplary embodiments with reference to the accompanying drawings, in which.

DETAILED DESCRIPTION

Figure 1:
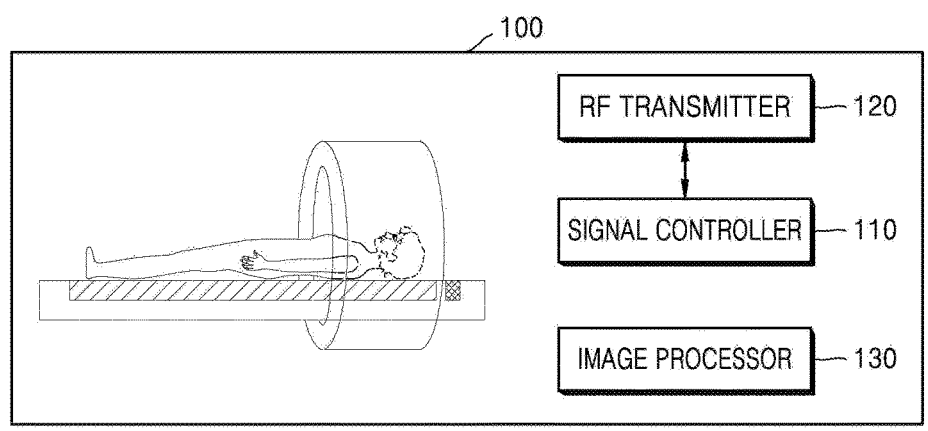
FIG. 1 is a block diagram of a medical imaging apparatus, according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions may not be described in detail because they would obscure the description with unnecessary detail.

When a part "includes" or "comprises" an element, unless there is a description contrary thereto, the part can further include other elements, not excluding the other elements. Also, the term "unit" in the exemplary embodiments of the inventive concept means a software component or hardware component such as a field-programmable gate array (FPGA) or an application-specific integrated circuit (ASIC), and performs a function. However, the term "unit" is not limited to software or hardware. The "unit" may be formed to be in an addressable storage medium, or may be formed to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units," or may be divided into additional components and "units."

In the present specification, an "image" may refer to multi-dimensional data composed of discrete image elements (e.g., pixels in a two-dimensional (2D) image and voxels in a three-dimensional (3D) image). For example, the image may be a medical image of an object captured by an X-ray apparatus, a computed tomography (CT) apparatus, a magnetic resonance imaging (MRI) apparatus, an ultrasound diagnosis apparatus, or another medical imaging apparatus.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. Furthermore, the "object" may be a phantom. The phantom means a material having a density, an effective atomic number, and a volume that are approximately the same as those of an organism. For example, the phantom may be a spherical phantom or a bottle-shaped phantom having properties similar to the human body.

Furthermore, in the present specification, a "user" may be, but is not limited to, a medical expert, such as a medical doctor, a nurse, a medical laboratory technologist, or a technician who repairs a medical apparatus.

Also, although examples of a medical imaging apparatus may include an X-ray apparatus, a CT apparatus, an MRI apparatus, an ultrasound diagnosis apparatus, and another medical imaging apparatus, the following will be explained for convenience on the assumption that a medical imaging apparatus is an MRI apparatus.

Furthermore, in the present specification, an "MR image" refers to an image of an object obtained by using the nuclear magnetic resonance principle.

Furthermore, in the present specification, a "pulse sequence" refers to continuity of signals repeatedly applied by an MRI apparatus. The pulse sequence may include a time parameter of a radio frequency (RF) pulse, for example, repetition time (TR) or echo time (TE).

Furthermore, in the present specification, a "pulse sequence schematic diagram" shows an order of events that occur in an MRI apparatus. For example, the pulse sequence schematic diagram may be a diagram showing an RF pulse, a gradient magnetic field, an MR signal, or the like according to time.

An MRI system is an apparatus for obtaining a sectional image of a part of an object by expressing, in a contrast comparison, a strength of a MR signal with respect to a radio frequency (RF) signal generated in a magnetic field having a strength. For example, if an RF signal that only resonates a specific atomic nucleus (for example, a hydrogen atomic nucleus) is emitted for an instant toward the object placed in a strong magnetic field and then such emission stops, an MR signal is emitted from the specific atomic nucleus, and thus the MRI system may receive the MR signal and obtain an MR image. The MR signal denotes an RF signal emitted from the object. An intensity of the MR signal may be determined according to a density of a predetermined atom (for example, hydrogen) of the object, a relaxation time T1, a relaxation time T2, and a flow of blood or the like.

MRI systems include characteristics different from those of other imaging apparatuses. Unlike imaging apparatuses such as CT apparatuses that obtain images according to a direction of detection hardware, MRI systems may obtain 2D images or 3D volume images that are oriented toward an optional point. MRI systems do not expose objects or examiners to radiation, unlike CT apparatuses, X-ray apparatuses, position emission tomography (PET) apparatuses, and single photon emission CT (SPECT) apparatuses, may obtain images having high soft tissue contrast, and may obtain neurological images, intravascular images, musculoskeletal images, and oncologic images that are used to precisely capture abnormal tissues.

As used herein, the term "and/or" includes any and all combinations of one or more of the associated listed items. Expressions such as "at least one of," when preceding a list of elements, modify the entire list of elements and do not modify the individual elements of the list.

FIG. 1 is a block diagram of a medical imaging apparatus 100, according to an exemplary embodiment.

Referring to FIG. 1, the medical imaging apparatus 100 according to an exemplary embodiment includes a signal controller 110, an RF transmitter 120, and an image processor 130.

The medical imaging apparatus 100 may refer to an apparatus for obtaining an MR image by using data obtained by a high-frequency multi-coil including a plurality of channel coils. In detail, the medical imaging apparatus 100 may receive a plurality of signals obtained by an RF coil that is the high-frequency multi-coil including the plurality of coils, and may generate an MR image by using the received plurality of signals.

In an exemplary embodiment, the signal controller 110 may generate pulse sequence information to control the RF transmitter 120, and may transmit the generated pulse sequence information to the RF transmitter 120. The pulse sequence information may include any information that is used to control the RF transmitter 120.

Also, the signal controller 110 may calculate flip angles respectively corresponding to RF refocusing pulses of a fast spin-echo (FSE) pulse sequence based on a pseudo-steady state model of a flip angle schedule.

The term 'FSE pulse sequence' may refer to a method of generating an MR image to generate a plurality of echoes during one TR by applying an RF excitation pulse and a plurality of RF refocusing pulses to an object during one TR.

The term 'echo' may refer to an MR signal obtained by the medical imaging apparatus 100, and echoes formed by using the FSE pulse sequence may be referred to as an echo train (ET). Accordingly, because the medical imaging apparatus 100 may obtain a plurality of echoes from the object during one TR, a scan time may be reduced. Also, a scan time of the FSE pulse sequence may be affected by an echo train length (ETL). The term 'ETL' may refer to the number of RF refocusing pulses applied to the object or the number of echoes generated during one TR.

Also, the term 'flip angle schedule' may refer to a pulse sequence including one or more RF refocusing pulses having variable flip angles that are experimentally determined. For example, the signal controller 110 may calculate 80 flip angles respectively corresponding to RF refocusing pulses of the FSE pulse sequence having 80 ETLs based on a pseudo-steady state model of a flip angle schedule including three RF refocusing pulses having three variable flip angles.

In an exemplary embodiment, a flip angle schedule may be determined when the medical imaging apparatus 100 is manufactured, and may be stored as a lookup table in a memory of the medical imaging apparatus 100 or in an external server.

A flip angle may depend on characteristics such as an RF coil, an RF pulse shape, and a duration, and may affect a MR image that is to be generated. In an exemplary embodiment, the signal controller 110 may use a different flip angle schedule according to a target tissue structure of an object to be scanned.

Accordingly, in an exemplary embodiment, the signal controller 110 may obtain from the memory a flip angle schedule including the RF refocusing pulses having a first flip angle, a second flip angle, a third flip angle based on the target tissue structure. However, an exemplary embodiment is not limited thereto, and the signal controller 110 may obtain a flip angle schedule including at least one RF refocusing pulse having a variable flip angle.

For example, when a target tissue structure is the brain, the signal controller 110 may obtain a flip angle schedule including three RF refocusing pulses having angles of 40°, 90°, and 120°. Also, in an exemplary embodiment, the signal controller 110 may receive a user input received by an input interface 181 of FIG. 2, and may correct, add, or delete the flip angle schedule.

Also, the signal controller 110 may determine an ETL in consideration of a contrast of an image that is to be generated and a scan time.

Also, the signal controller 110 may determine an ETL in response to a user input received from the input interface 181. For example, the signal controller 110 may determine an ETL according to a user input that selects a contrast of an image that is to be generated or a scan time.

Also, the signal controller 110 may divide an ET into a first ET interval and a second ET interval based on a target tissue structure.

For example, the signal controller 110 may determine an ETL as 80 based on a target tissue structure. In this case, when the target tissue structure is the brain, the signal controller 110 may divide 80 ETs into a first ET interval including 50 RF refocusing pulses and a second ET interval including 30 RF refocusing pulses. Alternatively, when the target tissue structure is a lung, the signal controller 110 may divide 80 ETs into a first ET interval including 40 RF refocusing pulses and a second ET interval including 40 RF refocusing pulses.

Alternatively, in an exemplary embodiment, the signal controller 110 may divide an ET excluding a first RF refocusing pulse having an angle of 180° into a first ET interval and a second ET interval. Alternatively, in an exemplary embodiment, the signal controller 110 may divide, but is not limited to, an ET excluding at least one RF refocusing pulse that is an RF refocusing pulse at the beginning of the ET into a first ET interval and a second ET interval. Also, when the target tissue structure is the brain, 50 RF refocusing pulses included in the first ET interval may have flip angles that are greater than a first flip angle (for example, 40°) and less than a second flip angle (for example, 90°). Also, 30 RF refocusing pulses included in the second ET interval may have flip angles that are greater than the second flip angle (for example, 90°) and less than a third flip angle (for example, 120°).

Also, the signal controller 110 may set that flip angles of RF refocusing pulses in each ET interval are linearly increased, based on a pseudo-steady state model of a flip angle schedule. Accordingly, the signal controller 110 may calculate a gradient corresponding to each ET interval based on flip angles of RF refocusing pulses corresponding to both ends of each ET interval. For example, the signal controller 110 may calculate a first gradient according to a first flip angle and a second flip angle of a flip angle schedule corresponding to both ends of a first ET interval, and may calculate a second gradient according to the second flip angle and a third flip angle of the flip angle schedule corresponding to both ends of a second ET interval.

Although the signal controller 110 divides an ET into two intervals in the above, an exemplary embodiment is not limited thereto. In an exemplary embodiment, the signal controller 110 may divide an ET into three or more intervals, or may use an ET as one interval. When the signal controller 110 divides an ET into three intervals, the signal controller 110 may calculate flip angles respectively corresponding to RF refocusing pulses based on three gradients respectively corresponding to the three intervals.

Also, the signal controller 110 may calculate flip angles respectively corresponding to RF refocusing pulses based on a first gradient and a second gradient.

In an exemplary embodiment, to prevent signal loss and sufficiently use available magnetization, the signal controller 110 may transmit to the RF transmitter 120 pulse sequence information for applying a first RF refocusing pulse having an angle of 180° to an object.

Also, the signal controller 110 may transmit pulse sequence information including RF refocusing pulses having calculated flip angles and an RF excitation pulse to the RF transmitter 120. The RF excitation pulse may refer to a pulse that non-selectively excites a signal at a predetermined part of an object to which the pulse is applied.

In an exemplary embodiment, the signal controller 110 may apply an RF excitation pulse having an angle of 90° to an object, and to prevent signal loss and sufficiently use available magnetization, may control the RF transmitter 120 to apply a first RF refocusing pulse having an angle of 180°, subsequent to the RF excitation pulse, to the object.

Figure 2:
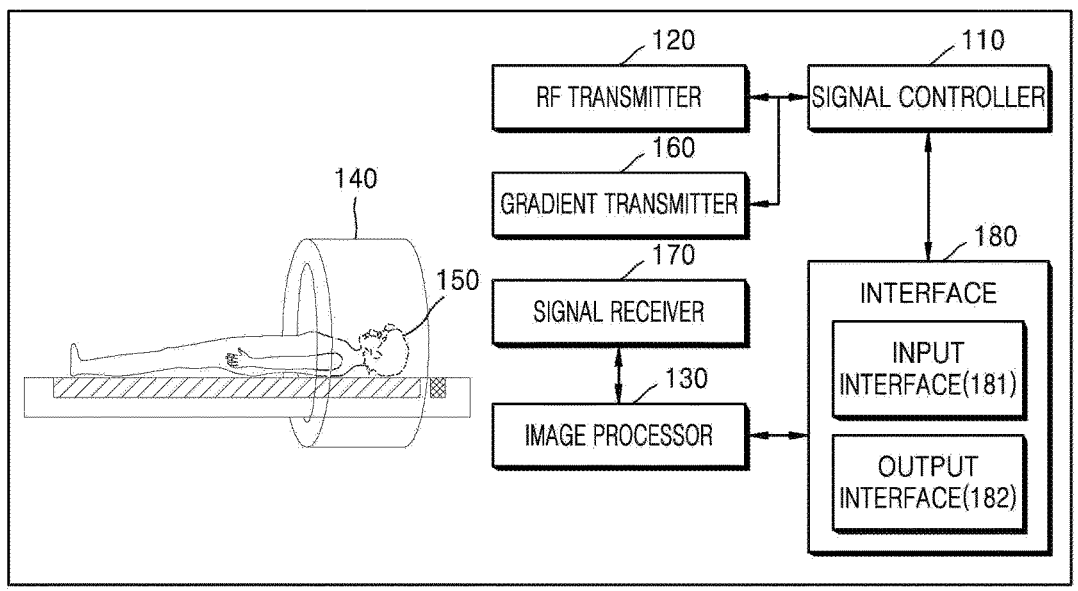
FIG. 2 is a block diagram of a medical imaging apparatus, according to another exemplary embodiment.

The RF transmitter 120 may drive an RF coil that is included in a gantry 140 of FIG. 2 according to a pulse sequence received from the signal controller 110. The RF transmitter 120 may supply an RF pulse at a Larmor frequency to the RF coil.

The image processor 130 may generate an MR image based on an MR signal received from an object.

FIG. 2 is a block diagram of the medical imaging apparatus 100, according to another exemplary embodiment.

As shown in FIG. 2, the medical imaging apparatus 100 according to an exemplary embodiment further includes a gradient transmitter 160, a signal receiver 170, and an interface 180 in addition to the signal controller 110, the RF transmitter 120, and the image processor 130 of FIG. 1.

The gantry 140 may prevent electromagnetic waves generated due to an RF coil and the like from being radiated to the outside. A static magnetic field and a gradient magnetic field may be formed in a bore in the gantry 140, and an RF signal may be emitted to an object 150.

According to an exemplary embodiment, the RF coil and the like may be arranged in a predetermined direction of the gantry 140. The predetermined direction may be a coaxial cylinder direction. The object 150 may be placed on a table that may be inserted into a cylinder along a horizontal axis of the cylinder.

As described above, the signal controller 110 may calculate flip angles respectively corresponding to RF refocusing pulses included in an FSE pulse sequence. A method of calculating flip angles has been described with reference to FIG. 1, and thus a detailed explanation thereof will not be given.

Also, the signal controller 110 may transmit to the RF transmitter 120 pulse sequence information including an RF excitation pulse and a plurality of RF refocusing pulses having calculated flip angles.

Also, the signal controller 110 may generate pulse sequence information for generating gradient magnetic fields along X, Y, and Z-axes, and may transmit the generated pulse sequence information to the gradient transmitter 160.

In an exemplary embodiment, the signal controller 110 may transmit to the gradient transmitter 160 pulse sequence information for applying diffusion gradient magnetic fields having the same size and the same direction to the object 150 before and after a first RF refocusing pulse is applied. Also, the signal controller 110 may control the gradient transmitter 160 to cause two diffusion gradient magnetic fields to be generated in X, Y, and Z-axes. Accordingly, when a contrast medium is injected into the object 150, the medical imaging apparatus 100 may selectively reduce an intensity of a signal obtained from blood flow in which the contrast medium is distributed based on the diffusion gradient magnetic fields.

The gradient transmitter 160 may drive a gradient coil included in the gantry 140 according to a pulse sequence received from the signal controller 110.

In an exemplary embodiment, the signal receiver 170 may receive from the gantry 140 an MR signal that is received from the object 150.

In an exemplary embodiment, when a contrast medium is injected into the object 150, the signal receiver 170 may obtain a signal having a reduced intensity from blood flow in which the contrast medium is distributed. In contrast, the signal receiver 170 may obtain a signal having an increased intensity from target tissue in which the contrast medium is accumulated.

The image processor 130 may generate an MR image based on the MR signal received from the signal receiver 170. The generated MR image may be an image having a high contrast between the target tissue and other tissue including the blood flow.

The interface 180 includes an output interface 182 and an input interface 181 that may enable the medical imaging apparatus 100 to communicate with a user.

In an exemplary embodiment, the input interface 181 may receive a user input that selects an ETL from the user. Also, the input interface 181 may receive a user input that corrects, adds, or deletes a flip angle schedule that is stored in a memory or an external server.

In an exemplary embodiment, the output interface 182 may display the MR image that is generated by the image processor 130. Also, the output interface 182 may divide the generated MR image into intervals according to an intensity of a signal obtained from the object 150, and may display the intervals.

Although the signal controller 110, the RF transmitter 120, the image processor 130, the gantry 140, the gradient transmitter 160, the signal receiver 170, and the interface 180 are separate elements in FIG. 2, functions performed by the signal controller 110, the RF transmitter 120, the image processor 130, the gantry 140, the gradient transmitter 160, the signal receiver 170, and the interface 180 may be performed by other elements.

Figure 3A:
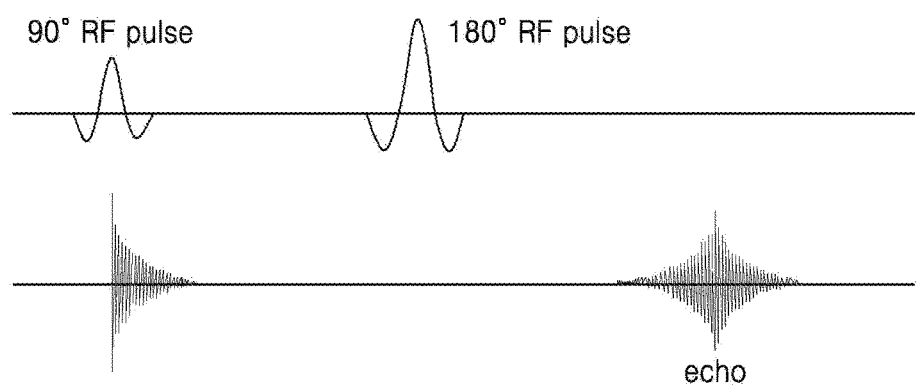
FIGS. 3A and 3B are diagrams for explaining a spin-echo (SE)
Figure 3B:
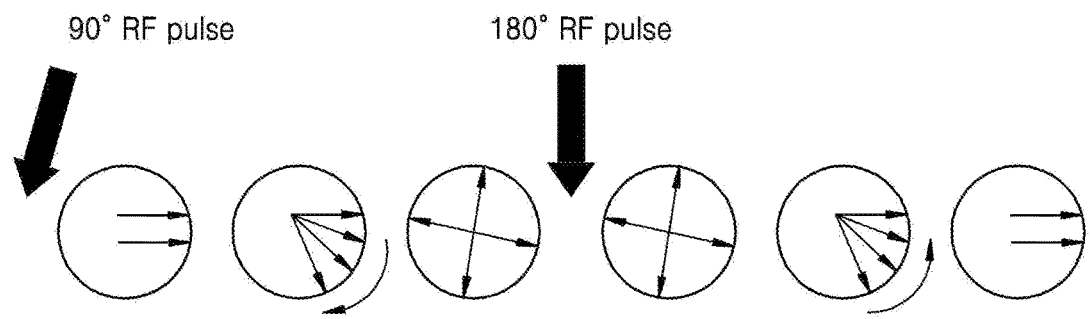

FIGS. 3A and 3B are diagrams for explaining a spin-echo (SE).

Referring to FIG. 3A, a pulse sequence schematic diagram of an SE includes an RF excitation pulse having an angle of 90° and an RF refocusing pulse having an angle of 180°. The term 'SE' may refer to a method of generating an MR image to generate one echo during one TR. The term 'echo' may refer to an MR signal that is obtained by the medical imaging apparatus 100.

In detail, as shown in FIG. 3B, the SE may refer to a method using magnetization in which when dephasing is performed for a predetermined period of time after an RF excitation pulse having an angle of 90° is applied to tissue, an RF refocusing pulse having an angle of 180° is applied so that hydrogen atoms process in phase in opposite directions.

Figure 3C:
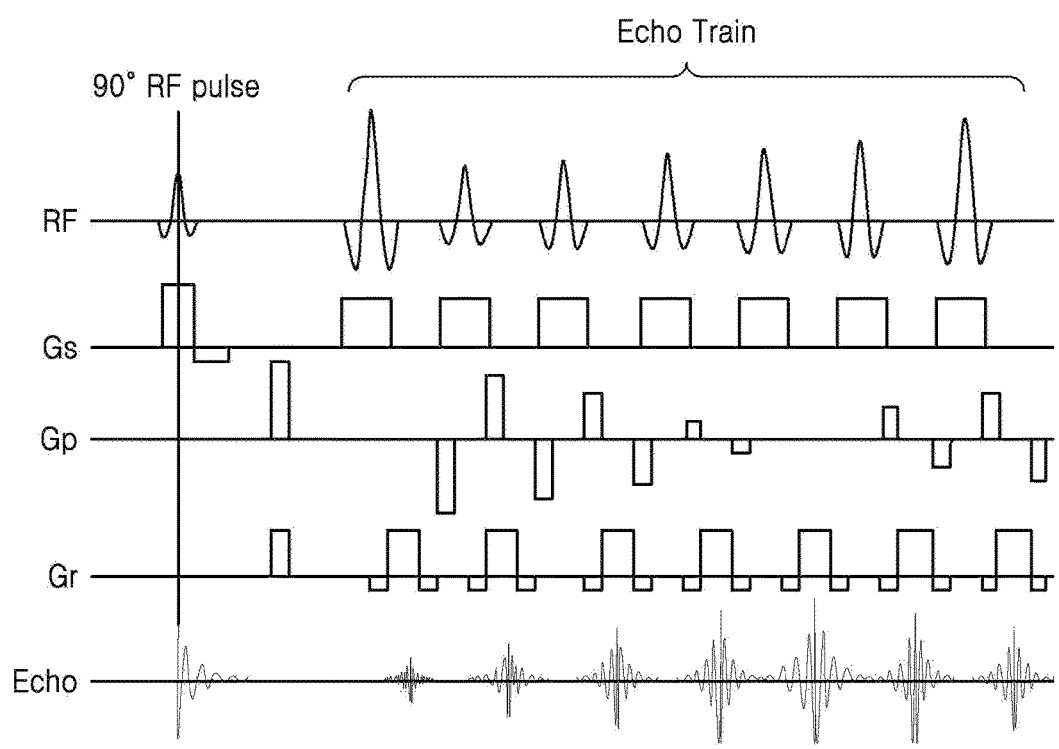
FIG. 3C is a pulse sequence schematic diagram of a fast spin-echo (FSE) pulse sequence including seven echo trains (ETs), according to an exemplary embodiment.

FIG. 3C is a pulse sequence schematic diagram of an FSE pulse sequence including seven ETs, according to an exemplary embodiment.

Referring to FIG. 3C, the FSE pulse sequence includes an RF excitation pulse having an angle of 90° and seven RF refocusing pulses having variable flip angles. In an exemplary embodiment, a flip angle of a first RF refocusing pulse may be 180°.

In an exemplary embodiment, the medical imaging apparatus 100 may apply to the object 150 RF refocusing pulses having variable flip angles according to a target tissue structure based on a pseudo-steady state model of a flip angle schedule. Accordingly, the medical imaging apparatus 100 may reduce a scan time and may generate an MR image having a high contrast between target tissue and other tissue.

Figure 4:
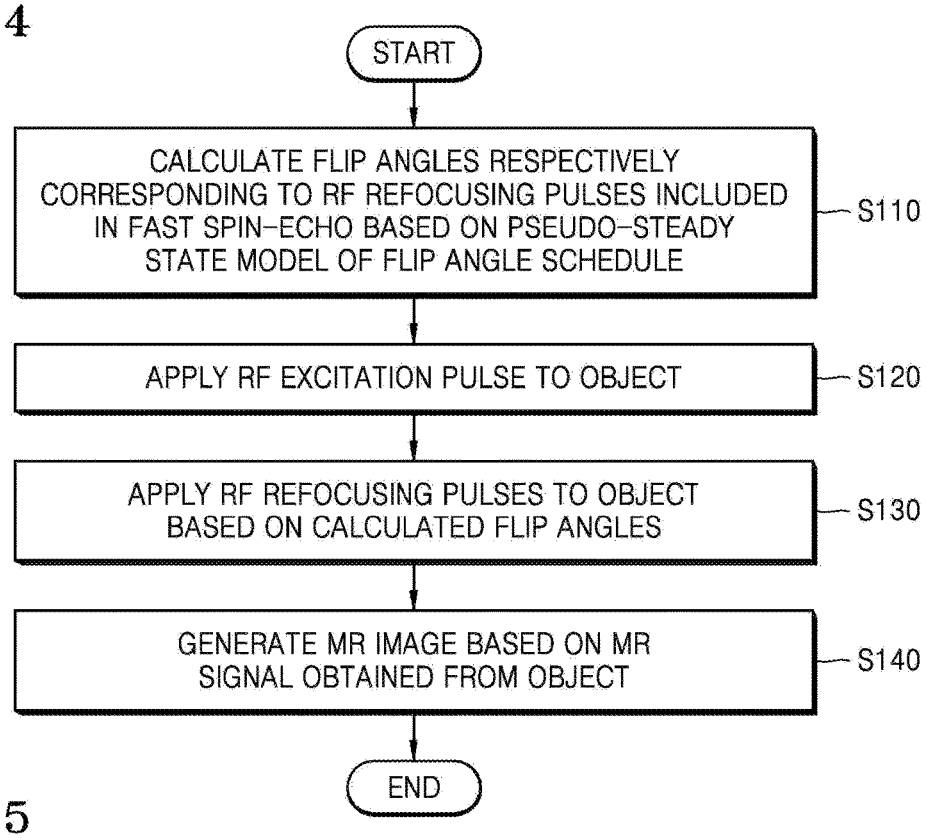
FIG. 4 is a flowchart of a method performed by a medical imaging apparatus to generate an image, according to an exemplary embodiment.

FIG. 4 is a flowchart performed by the medical imaging apparatus 100 to generate an image, according to an exemplary embodiment.

Referring to FIG. 4, in operation S110, the medical imaging apparatus 100 calculates flip angles respectively corresponding to RF refocusing pulses included in an FSE pulse sequence, based on a pseudo-steady state model of a flip angle schedule.

As described above, the FSE pulse sequence may refer to a method of generating an MR image to generate a plurality of echoes during one TR by applying an RF excitation pulse and a plurality of RF refocusing pulses to the object 150 during one TR.

The medical imaging apparatus 100 may reduce a scan time by adjusting an ETL of the FSE pulse sequence. The term 'ETL' may refer to the number of RF refocusing pulses applied to the object 150 during one TR.

Also, the term 'flip angle schedule' may refer to a pulse sequence including at least one RF refocusing pulse having a variable flip angle. For example, the medical imaging apparatus 100 may calculate 80 flip angles respectively corresponding to RF refocusing pulses of an FSE pulse sequence having 80 ETLs based on a pseudo-steady state model of a flip angle schedule including three RF refocusing pulses having three variable flip angles.

In an exemplary embodiment, a flip angle schedule may be determined when the medical imaging apparatus 100 is manufactured, and may be stored as a lookup table in the medical imaging apparatus 100 or an external server.

A flip angle may depend on characteristics such as an RF coil, an RF pulse shape, or a duration, and may affect an MR image that is to be generated. In an exemplary embodiment, the medical imaging apparatus 100 may use a different flip angle schedule according to a target tissue structure of the object 150 to be scanned.

Accordingly, in an exemplary embodiment, the medical imaging apparatus 100 may obtain a flip angle schedule including three RF refocusing pulses having a first flip angle, a second flip angle, and a third flip angle based on a target tissue structure. However, an exemplary embodiment is not limited thereto, and the medical imaging apparatus 100 may obtain a flip angle schedule including at least one RF refocusing pulse having a variable flip angle.

For example, when the target tissue structure is the brain, the medical imaging apparatus 100 may obtain a flip angle schedule including three RF refocusing pulses having angles of 40°, 90°, and 120°.

Also, in an exemplary embodiment, the medical imaging apparatus 100 may correct, add, or delete the flip angle schedule based on a user input for the flip angle schedule.

Also, in an exemplary embodiment, the medical imaging apparatus 100 may set a pseudo-steady state model of the flip angle schedule. For example, the medical imaging apparatus 100 may divide an ET of an FSE pulse sequence into a plurality of intervals based on RF refocusing pulses included in the flip angle schedule, and may set so that flip angles respectively corresponding to the RF refocusing pulses of the FSE pulse sequence included in each interval are linearly increased. A method of calculating a pseudo-steady state model of a flip angle schedule and flip angles corresponding to each ET will be explained below with reference to FIGS. 5 and 6.

In an exemplary embodiment, the medical imaging apparatus 100 may determine an ETL in consideration of a contrast of an image that is to be generated and a scan time.

Also, the medical imaging apparatus 100 may determine an ETL in response to the user's input. For example, the medical imaging apparatus 100 may receive a user input that selects a contrast of an image that is to be generated or a scan time. The medical imaging apparatus 100 may determine the ETL according to the received user input.

The medical imaging apparatus 100 may reduce a scan time as an ETL increases. However, the medical imaging apparatus 100 may generate an image with ringing artifacts due to a phase error or a blurred image as an ETL increases. Accordingly, the medical imaging apparatus 100 may generate an image whose signal-to-noise ratio (SNR) and contrast are reduced. Accordingly, the medical imaging apparatus 100 may determine an appropriate ETL in response to the user's input.

In operation S120, the medical imaging apparatus 100 applies an RF excitation pulse to the object 150. The term 'RF excitation pulse' may refer to a pulse that non-selectively excites a signal at a predetermined part of the object 150 to which the pulse is applied. For example, the medical imaging apparatus 100 may apply an RF excitation pulse having an angle of 90° to the object 150.

In operation S130, the medical imaging apparatus 100 applies a plurality of RF refocusing pulses to the object 150 based on the calculated flip angles. In an exemplary embodiment, the medical imaging apparatus 100 may apply a first RF refocusing pulse having an angle of 180° to the object 150 to prevent signal loss and sufficiently use available magnetization.

In an exemplary embodiment, the medical imaging apparatus 100 may inject a contrast medium into the object 150. Once the contrast medium is injected into the object 150, the contrast medium may be accumulated in target tissue. Accordingly, the medical imaging apparatus 100 may obtain an image whose contrast between the target tissue and other tissue is increased.

However, because the contrast medium may also increase a contrast of both the target tissue and a blood vessel in which the contrast medium is distributed, the accuracy of detecting the target tissue may be reduced. Accordingly, in an exemplary embodiment, the medical imaging apparatus 100 may generate an image whose contrast of target tissue (e.g., cancer tissue) is selectively increased by using a diffusion gradient magnetic field. In an exemplary embodiment, to distinguish the target tissue, the medical imaging apparatus 100 may add a diffusion gradient magnetic field to gradient magnetic fields in X, Y, and Z-axis directions before and after a first RF refocusing pulse is applied. In this case, the medical imaging apparatus 100 may obtain a signal whose intensity is increased from the target issue and a signal whose intensity is reduced from blood flow. Accordingly, the medical imaging apparatus 100 may generate an image of a target tissue structure in which a signal obtained from the blood flow is suppressed. A method performed by the medical imaging apparatus 100 to generate an image so that a signal obtained from blood blow is suppressed will be explained below with reference to FIG. 5.

In operation S140, the medical imaging apparatus 100 generates an MR image based on an MR signal obtained from the object 150. Also, the medical imaging apparatus 100 may display the generated MR image.

In an exemplary embodiment, the medical imaging apparatus 100 may divide the MR image into intervals according to an intensity of a signal that is obtained, and may display the intervals. For example, the medical imaging apparatus 100 may divide an image corresponding to the target tissue (e.g., cancer tissue) whose signal intensity is high into intervals, and may display the intervals. Accordingly, the medical imaging apparatus may reduce a time taken for the user to interpret the image to distinguish the target tissue.

Figure 5:
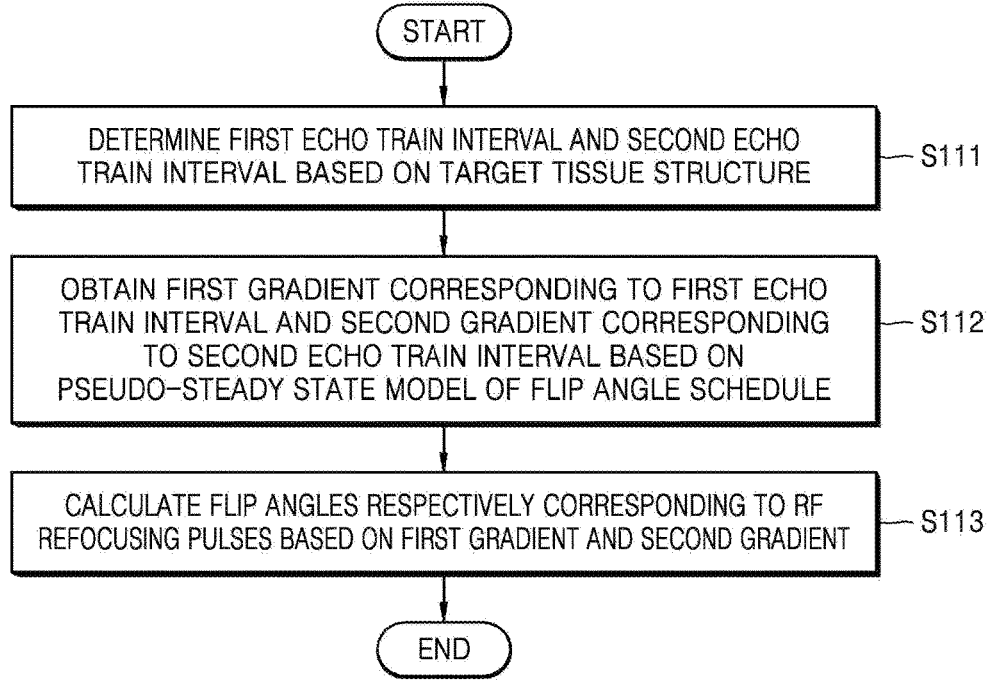
FIG. 5 is a flowchart of a method of calculating a variable flip angle of an FSE pulse sequence, according to an exemplary embodiment.

FIG. 5 is a flowchart of a method of calculating a variable flip angle of an FSE pulse sequence, according to an exemplary embodiment.

Referring to FIG. 5, in operation S111, the medical imaging apparatus 100 divides an ET of an FSE pulse sequence into a first ET interval and a second ET interval (i.e., determines the first ET interval and the second ET interval) based on a target tissue structure.

For example, the medical imaging apparatus 100 may determine an ETL as 80 based on the target tissue structure. In this case, when the target tissue structure is the brain, the medical imaging apparatus 100 may divide 80 ETs into a first ET interval including 50 RF refocusing pulses and a second ET interval including 30 RF refocusing pulses. Alternatively, when the target tissue structure is a lung, the medical imaging apparatus 100 may divide 80 ETs into a first ET interval including 40 RF refocusing pulses and a second ET interval including 40 RF refocusing pulses. Alternatively in an exemplary embodiment, the medical imaging apparatus 100 may divide an ET excluding a first RF refocusing pulse having an angle of 180° into a first ET interval and a second ET interval. Alternatively, the medical imaging apparatus 100 may divide an ET excluding at least one RF refocusing pulse at the beginning of the ET into a first ET interval and a second ET interval. However, an exemplary embodiment is not limited thereto.

As described above, a flip angle schedule obtained by the medical imaging apparatus 100 may include three RF refocusing pulses having a first flip angle, a second flip angle, and a third flip angle based on the target tissue structure. For example, when the target tissue structure is the brain, the flip angle schedule may include three RF refocusing pulses having angles of 40°, 90°, and 120°.

Also, when the target tissue structure is the brain, 50 RF refocusing pulses included in the first ET interval may have flip angles that are greater than a first flip angle (e.g., 40°) and less than a second flip angle (e.g., 90°) of the flip angle schedule. Also, 30 RF refocusing pulses included in the second ET interval may have flip angles that are greater than the second flip angle (e.g., 90°) and less than a third flip angle (e.g., 120°) of the flip angle schedule.

In operation S112, the medical imaging apparatus 100 obtains a first gradient corresponding to the first ET interval and a second gradient corresponding to the second ET interval, based on a pseudo-steady state model of the flip angle schedule.

In an exemplary embodiment, the medical imaging apparatus 100 may set based on the pseudo-steady state model of the flip angle schedule so that flip angles of RF refocusing pulses in each ET interval are linearly increased. Also, the pseudo-steady state model of the flip angle schedule may be represented as a graph having an ETL as an X-axis. For example, the medical imaging apparatus 100 may calculate a gradient of each ET interval based on flip angles of RF refocusing pulses corresponding to both ends of each ET interval.

Figure 6:
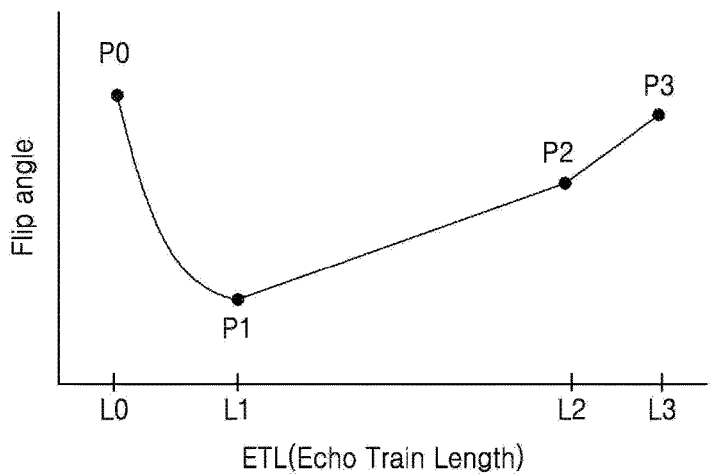
FIG. 6 is a graph according to a pseudo-steady state model of a flip angle schedule, according to an exemplary embodiment.

FIG. 6 is a graph according to a pseudo-steady state model of a flip angle schedule, according to an exemplary embodiment.

Referring to FIG. 6, the graph according to the pseudo-steady state model of the flip angle schedule is a graph that linearly connects a first flip angle P1, a second flip angle P2, and a third flip angle P3 of RF refocusing pulses included in the flip angle schedule.

Also, when an ET is divided into a first ET interval and a second ET interval, the first ET interval may correspond to an interval L1-L2 of the graph, and the second ET interval may correspond to an interval L2-L3 of the graph.

Accordingly, the medical imaging apparatus 100 may calculate a first gradient corresponding to the first ET interval based on the first flip angle P1 and the second flip angle P2 respectively corresponding to both end points L1 and L2 of the first ET interval. Also, the medical imaging apparatus 100 may calculate a second gradient based on the second flip angle P2 and the third flip angle P3 respectively corresponding to both end points L2 and L3 of the second ET interval.

Also, in an exemplary embodiment, P0 corresponds to a first RF refocusing pulse of an FSE pulse sequence.

Referring back to FIG. 5, in operation S113, the medical imaging apparatus 100 calculates flip angles respectively corresponding to RF refocusing pulses based on the first gradient and the second gradient.

Although the medical imaging apparatus 100 divides an ET into two intervals in the above, an exemplary embodiment is not limited thereto. In an exemplary embodiment, the medical imaging apparatus 100 may divide an ET into three or more intervals, or may use an ET as one interval. When the medical imaging apparatus 100 divides an ET into three or more intervals, the medical imaging apparatus 100 may calculate a flip angle corresponding to each RF refocusing pulse based on a gradient corresponding to each interval.

Figure 7:
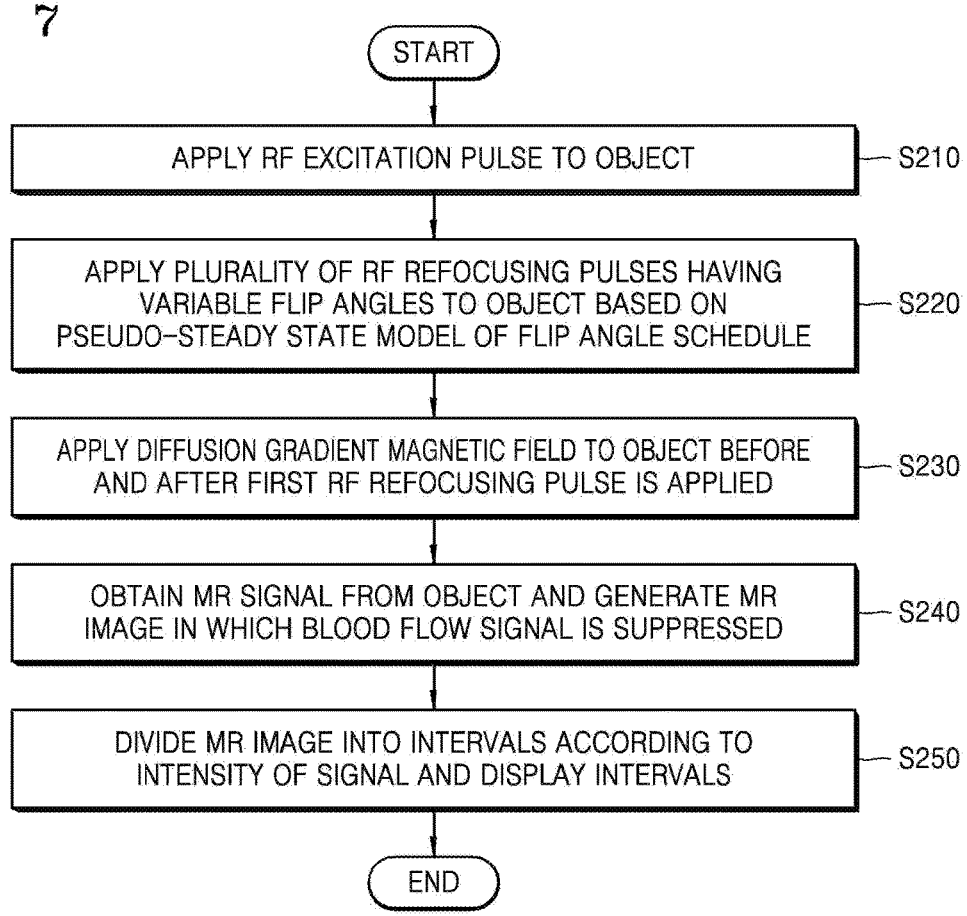
FIG. 7 is a flowchart of a method of generating a magnetic resonance (MR) image in which a signal obtained from blood flow is suppressed, according to an exemplary embodiment.

FIG. 7 is a flowchart of a method of generating an MR signal in which a signal obtained from blood flow is suppressed, according to an exemplary embodiment.

Referring to FIG. 7, in operation S210, the medical imaging apparatus 100 applies an RF excitation pulse to the object 150.

In operation S220, the medical imaging apparatus 100 applies a plurality of RF refocusing pulses having variable flip angles to the object 150 based on a pseudo-steady state model of a flip angle schedule. A method performed by the medical imaging apparatus 100 to calculate a variable flip angle based on a pseudo-steady state model of a flip angle schedule has been described with reference to FIG. 5, and thus a detailed explanation thereof will not be given.

In operation S230, the medical imaging apparatus 100 generates pulse sequence information to generate and apply a diffusion gradient magnetic field to the object 150 in gradient magnetic fields in X, Y, and Z-axis directions before and after a first refocusing pulse is applied.

Figure 8:
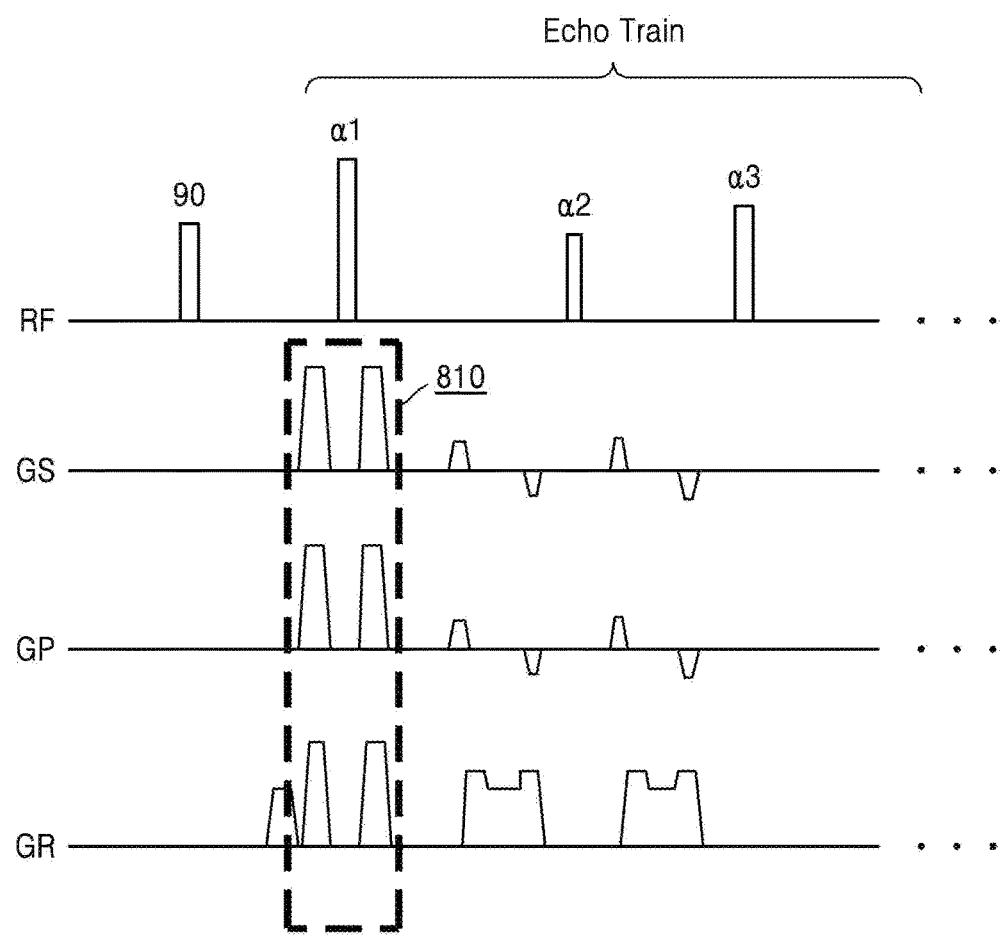
FIG. 8 is a pulse sequence schematic diagram, according to an exemplary embodiment.

FIG. 8 is a pulse sequence schematic diagram, according to an exemplary embodiment.

Referring to FIG. 8, the medical imaging apparatus 100 generates diffusing gradients 810 having the same size and the same direction in a slice gradient magnetic field GS, a phase gradient magnetic field GP, and a readout gradient magnetic field GR before and after a first refocusing pulse al is applied. The slice gradient magnetic field GS, the phase gradient magnetic field GP, and the readout gradient magnetic field GR may correspond to the gradient magnetic fields in the X, Y, and Z-axis directions of the medical imaging apparatus 100.

Because the medical imaging apparatus 100 according to an exemplary embodiment applies a diffusion gradient magnetic field to the object 150 before and after the first refocusing pulse is applied, phase dispersion according to magnetization of blood flow from the beginning of an ET may be increased. Also, because the medical imaging apparatus 100 adds the diffusion gradient magnetic field to gradient magnetic fields in X, Y, and Z-axis directions irrespective of a direction of the blood flow, reduce an intensity of a signal obtained from the blood flow may be rapidly reduced.

Referring back to operation S240 of FIG. 7, the medical imaging apparatus 100 obtains an MR signal from the object 150.

In an exemplary embodiment, when a contrast medium is injected into the object 150, the medical imaging apparatus 100 may obtain an MR signal whose intensity is reduced from blood flow due to the diffusion gradient magnetic field applied to the object 150. In contrast, the medical imaging apparatus 100 may obtain an MR signal whose intensity is increased from target tissue.

Accordingly, the medical imaging apparatus 100 generates an MR image having a high contrast between the target tissue and other tissue including the blood flow, i.e., an MR image in which a blood flow signal is suppressed.

In operation S250, the medical imaging apparatus 100 divides the MR image into intervals according to an intensity of a signal that is obtained, and displays the intervals. In an exemplary embodiment, the medical imaging apparatus 100 may obtain a signal whose intensity is increased from the target tissue due to the contrast medium injected into the object 150. Accordingly, the medical imaging apparatus 100 may divide and display an image of the target tissue according to an intensity of a signal that is obtained. Because the medical imaging apparatus 100 displays the divided image, a time taken for the user to interpret the MR image may be reduced.

Figure 9:
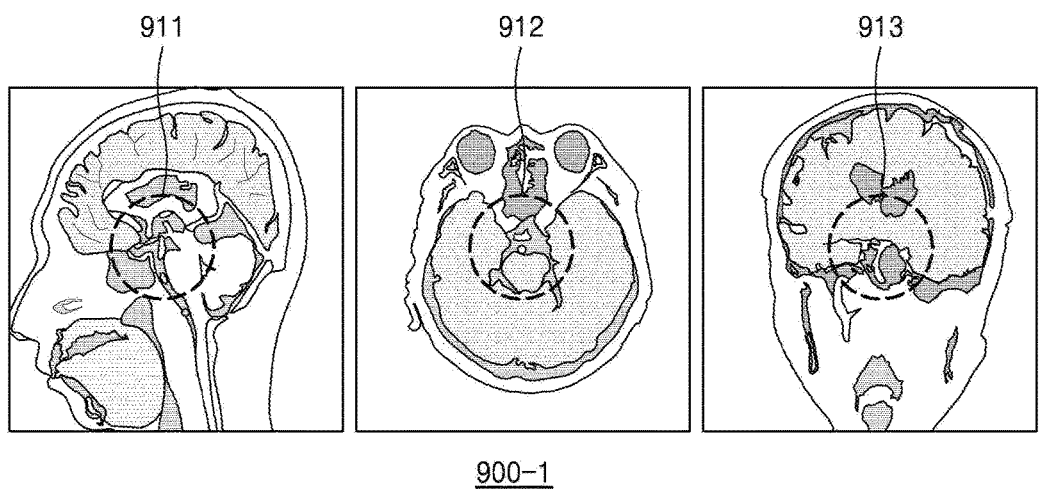
FIG. 9 is a view illustrating an MR image that is generated by the medical imaging apparatus, according to an exemplary embodiment.
Figure 9:
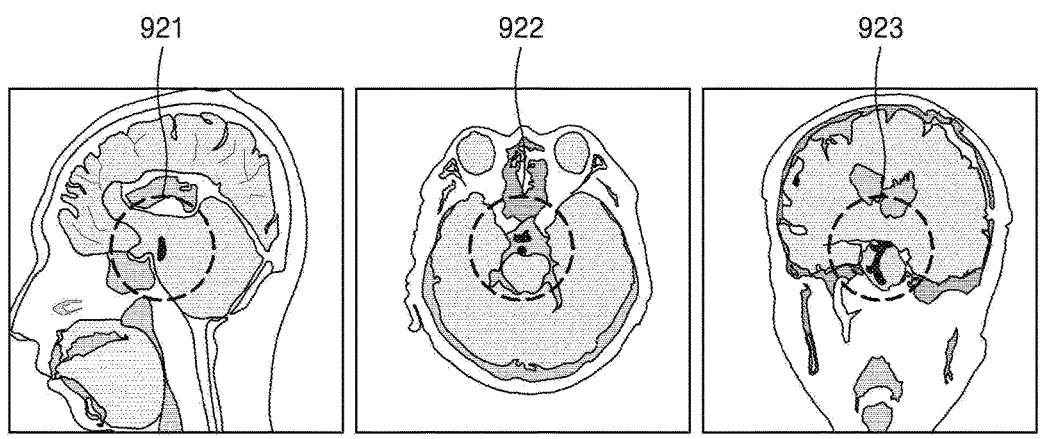

FIG. 9 is a view illustrating an MR image that is generated by the medical imaging apparatus 100, according to an exemplary embodiment.

Referring to FIG. 9, the medical imaging apparatus 100 may generate an MR image in which an intensity of a signal obtained from a target tissue structure is selectively increased by injecting a contrast medium into the object 150. In an exemplary embodiment, the medical imaging apparatus 100 may generate an MR image by using an FSE pulse sequence based on a pseudo-steady state model of a flip angle schedule.

Referring to portion 900-1, the medical imaging apparatus 100 may obtain a signal whose intensity is relatively increased from target tissue in which the contrast medium is accumulated and from blood flow in which the contrast medium is distributed. Accordingly, the medical imaging apparatus 100 generates images 911, 912, and 913 in which both the blood flow and the target tissue are enhanced.

Accordingly, the medical imaging apparatus 100 may add a diffusion gradient magnetic field for reducing magnetization of blood to gradient magnetic fields in X, Y, and Z-axis directions before and after a first RF refocusing pulse of the FSE pulse sequence is applied. Referring to portion 900-2, the medical imaging apparatus 100 generates MR images 921, 922, and 923 in which the blood flow is suppressed by adding the diffusion gradient magnetic field to the gradient magnetic fields in the X, Y, and Z-axis directions.

Figure 10:
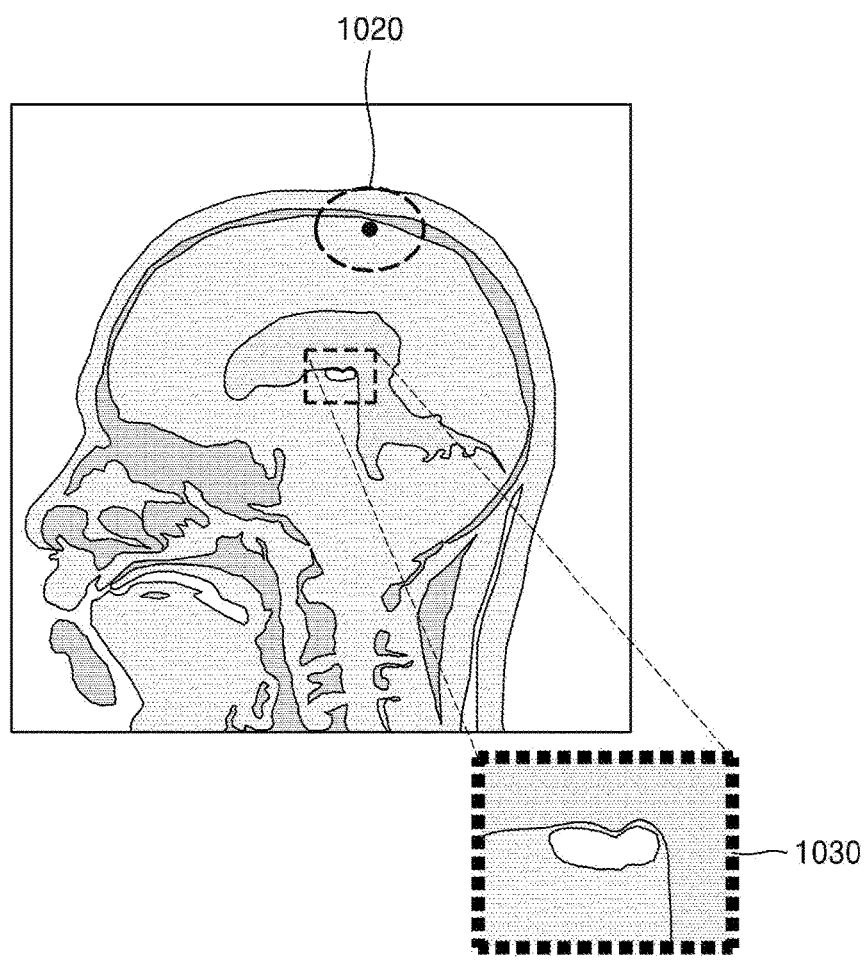
FIG. 10 is a view for explaining a process of dividing an MR image into intervals according to an intensity of a signal that is obtained, and displaying the intervals, according to an exemplary embodiment.

FIG. 10 is a view for explaining a process of dividing an MR image into intervals according to an intensity of a signal that is obtained, and displaying the intervals, according to an exemplary embodiment.

Referring to FIG. 10, the medical imaging apparatus 100 may divide an MR image into intervals according to an intensity of a signal that is obtained, and may display the intervals.

In an exemplary embodiment, the medical imaging apparatus 100 generates an image 1020 of blood flow an intensity of a signal obtained from which is reduced by generating a diffusion gradient magnetic field in gradient magnetic fields in X, Y, and Z-axis directions. Accordingly, the medical imaging apparatus 100 may obtain a signal having a high intensity from target tissue according to a contrast medium injected into the object 150. Also, the medical imaging apparatus 100 may generate an image having a high contrast for the target tissue.

Also, in an exemplary embodiment, the medical imaging apparatus 100 divides an image 1030 obtained by enlarging the target tissue into intervals according to an intensity of a signal that is obtained and may display the intervals. Alternatively, in an exemplary embodiment, the medical imaging apparatus 100 may divide the target tissue with a signal having a high intensity into cross-sections in various directions and may display the cross-sections.

Also, in an exemplary embodiment, the medical imaging apparatus 100 may, but is not limited to, highlight and display the target disuse with the signal having the high intensity.

As such, because the medical imaging apparatus 100 according to an exemplary embodiment divides an MR image into intervals according to an intensity of a signal that is obtained and displays the intervals, a time taken for the user to interpret the MR image with naked eyes may be reduced.

Figure 11:
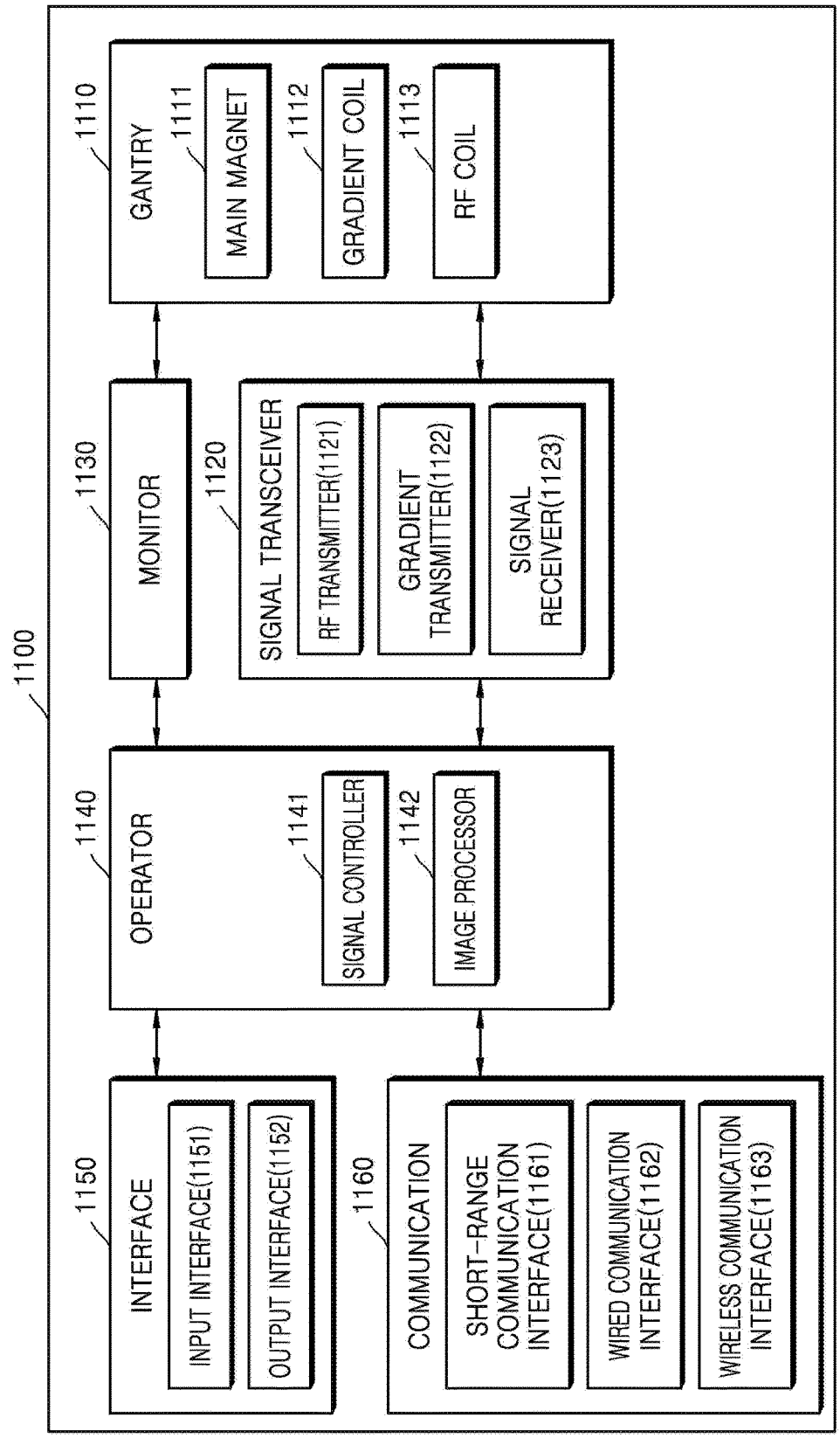
FIG. 11 is a block diagram of a medical imaging apparatus, according to another exemplary embodiment.

FIG. 11 is a block diagram of a medical imaging apparatus 1100, according to another exemplary embodiment.

The medical imaging apparatus 1100 according to an exemplary embodiment includes a signal transceiver 1120, an operator 1140, a gantry 1110, and an interface 1150. Also, the medical imaging apparatus 1100 according to an exemplary embodiment further includes a monitor 1130 and a communication interface 1160.

The gantry 1110 includes a main magnet 1111, a gradient coil 1112, and an RF coil 1113, and prevents external emission of electromagnetic waves generated by the main magnet 1111, the gradient coil 1112, and the RF coil 1113. A static magnetic field and a gradient magnetic field are formed in a bore in the gantry 1110, and an RF signal is emitted to an object. The gantry is respectively corresponding to the gantry 140 of FIG. 2.

The main magnet 1111, the gradient coil 1112, and the RF coil 1113 may be arranged in a predetermined direction of the gantry 1110. The predetermined direction may be a coaxial cylinder direction. Also, the gantry 1110 may include a table on which the object is placed.

The main magnet 1111 generates a static magnetic field for aligning magnetic dipole moments of atomic nuclei of the object in a constant direction. A more precise and accurate MR image of the object may be obtained as a magnetic field generated by the main magnet 1111 is stronger and more uniform.

The gradient coil 1112 includes X, Y, and Z coils for generating gradient magnetic fields in X-, Y-, and Z-axis directions crossing each other at right angles. The gradient coil 1112 may provide location information of each region of the object by differently inducing resonance frequencies according to the regions of the object.

The RF coil 1113 may emit an RF signal to the object and receive an MR signal emitted from the object. In detail, the RF coil 1113 may transmit, to atomic nuclei included in the object and having a precessional motion, an RF signal having the same frequency as that of the precessional motion, stop transmitting the RF signal, and then receive an MR signal emitted from the atomic nuclei included in the object.

For example, to transit an atomic nucleus from a low energy state to a high energy state, the RF coil 1113 may generate and apply an electromagnetic wave signal that is an RF signal corresponding to a type of the atomic nucleus, to the object. When the electromagnetic wave signal generated by the RF coil 1113 is applied to the atomic nucleus, the atomic nucleus may transit from the low energy state to the high energy state. Then, when electromagnetic waves generated by the RF coil 1113 disappear, the atomic nucleus to which the electromagnetic waves were applied transits from the high energy state to the low energy state, thereby emitting electromagnetic waves having a Larmor frequency. In other words, when the applying of the electromagnetic wave signal to the atomic nucleus is stopped, an energy level of the atomic nucleus is changed from a high energy level to a low energy level, and thus the atomic nucleus may emit electromagnetic waves having a Larmor frequency. The RF coil 1113 may receive electromagnetic wave signals from atomic nuclei included in the object.

The RF coil 1113 may be realized as one RF transmitting and receiving coil having both a function of generating electromagnetic waves each having an RF that corresponds to a type of an atomic nucleus and a function of receiving electromagnetic waves emitted from an atomic nucleus. Alternatively, the RF coil 26 may be realized as a transmission RF coil having a function of generating electromagnetic waves each having an RF that corresponds to a type of an atomic nucleus, and a reception RF coil having a function of receiving electromagnetic waves emitted from an atomic nucleus.

The RF coil 1113 may be fixed to the gantry 1110 or may be detachable. When the RF coil 1113 is detachable, the RF coil 26 may be an RF coil for a part of the object, such as a head RF coil, a chest RF coil, a leg RF coil, a neck RF coil, a shoulder RF coil, a wrist RF coil, or an ankle RF coil.

The RF coil 1113 may communicate with an external apparatus via wires and/or wirelessly, and may also perform dual tune communication according to a communication frequency band.

The RF coil 1113 may be a birdcage coil, a surface coil, or a transverse electromagnetic (TEM) coil according to structures. The RF coil 1113 may be a transmission exclusive coil, a reception exclusive coil, or a transmission and reception coil according to methods of transmitting and receiving an RF signal. The RF coil 1113 may be an RF coil having various numbers of channels, such as 16 channels, 32 channels, 72 channels, and 144 channels.

The gantry 1110 may further include a display disposed inside and outside the gantry 1110. The medical imaging apparatus 1100 may provide predetermined information to the user or the object through the display disposed outside and inside the gantry 1110.

An RF transmitter 1121 may drive the RF coil 1113. The RF transmitter 1121 may supply an RF pulse at a Larmor frequency to the RF coil 1113. The RF transmitter 1121 is respectively corresponding to the RF transmitter 120 of FIG. 1.

In an exemplary embodiment, the RF transmitter 1121 may supply an RF excitation pulse and a plurality of RF refocusing pulses having variable flip angles to the RF coil 1113 during one TR.

A gradient transmitter 1122 may drive the gradient coil 1112 that is included in the gantry 1110, and may supply a pulse signal for generating a gradient magnetic field to the gradient coil 1112 under the control of the operator 1140. The signal transceiver 1120 may combine gradient magnetic fields in X, Y, and Z-axis directions by controlling a pulse signal supplied to the gradient coil 1112. The gradient transmitter 1122 is respectively corresponding to the gradient transmitter 160 of FIG. 2.

In an exemplary embodiment, the gradient transmitter 1122 may supply to the gradient coil 1112 a pulse signal for generating a diffusion gradient magnetic field in gradient magnetic fields in X, Y, and Z-axis directions before and after a first refocusing pulse is applied within one TR.

The signal receiver 1122 may receive an MR signal that is received by the RF coil 1113.

Also, the signal transceiver 1120 may adjust transmitting and receiving directions of an RF signal and an MR signal. For example, the RF signal may be emitted to the object through the RF coil 1113 during a transmission mode, and the MR signal may be received from the object through the RF coil 1113 during a reception mode. The signal transceiver 1120 may adjust the transmitting and receiving directions of the MR signal and the RF signal by using a control signal from the operator 1140.

The monitor 1130 may monitor or control the gantry 1110 or devices mounted on the gantry 1110.

The monitor 1130 may monitor and control a state of a static magnetic field, a state of a gradient magnetic field, a state of an RF signal, a state of the RF coil 1113, a state of the table, a state of a device for measuring body information of the object, a power supply state, a state of a thermal exchanger, and a state of a compressor.

Also, the monitor 1130 may monitor a state of the object. In detail, the monitor 1130 may include a camera for observing a movement or position of the object, a respiration measurer for measuring the respiration of the object, an electrocardiogram (ECG) measurer for measuring the electrical activity of the object, or a temperature measurer for measuring a temperature of the object.

Also, the monitor 1130 may control the table on which the object is placed to be moved. For example, during moving imaging of the object, the monitor 1130 may continuously or discontinuously move the table according to the sequence control of the operator 1140, and thus the object may be photographed in a field of view (FOV) larger than that of the gantry 1110.

Also, the monitor 1130 may control a display that is disposed inside and outside the gantry 1110. For example, the monitor 1130 may control the display to be turned on or off or a screen output to the display.

The operator 1140 may control an overall operation of the medical imaging apparatus 1100. Also, the operator 1140 includes a signal controller 1141 that generates pulse sequence information and an image processor 1142 that processes an MR signal received from the signal transceiver 1120. The signal controller 1141 and the image processor 1142 are respectively corresponding to the signal controller 120 and the image process 130 of FIG. 1.

The signal controller 1141 may control a sequence of signals for controlling the gantry 1110 and devices mounted on the gantry 1110. Also, the signal controller 1141 may generate pulse sequence information for controlling the signal transceiver 1120 and may transmit the generated pulse sequence information to the signal transceiver 1120. The term 'pulse sequence information' may include any information that is used to control the signal transceiver 1120. For example, the pulse sequence information may include information about a size of a pulse signal applied to the gradient coil 1112, a time for which the pule signal is applied, and a time at which the pulse signal is applied. Also, in an exemplary embodiment, the signal controller 1141 may calculate variable flip angles corresponding to RF refocusing pulses of an FSE pulse sequence based on a pseudo-steady state model of a flip angle schedule. Accordingly, the medical imaging apparatus 100 may reduce a scan time.

For example, the signal controller 1141 may divide an ET of the FSE pulse sequence into a first ET interval and a second ET interval based on a target tissue structure. Also, flip angles of RF refocusing pulses corresponding to a start point and an end point of each ET interval may be flip angles of RF refocusing pulses included in the flip angle schedule. Also, the signal controller 1141 may calculate a flip angle corresponding to each ET based on a gradient corresponding to each ET interval.

Also, the signal controller 1141 may determine an ETL in consideration of a contrast of an image that is to be generated and a scan time.

Also, the signal controller 1141 may transmit to the signal transceiver 1120 a pulse sequence including an RF excitation pulse and a plurality of RF refocusing pulses having calculated flip angles during one TR. In an exemplary embodiment, the signal controller 1141 may transmit to the RF transmitter 1121 pulse sequence information for applying a first RF refocusing pulse having an angle of 180° to the object, to prevent signal loss and sufficiently use available magnetization.

Also, the signal controller 1141 may transmit to the signal transceiver 1120 a pulse sequence for applying diffusion gradient magnetic fields having the same size and the same direction to the object before and after the first RF refocusing pulse is applied.

Also, the signal controller 1141 may generate a signal for amplifying a signal obtained from the gantry 1110 and may transmit the generated signal to the signal transceiver 1120. For example, the signal controller 1141 may generate various signals to perform various processing, such as frequency transformation, phase detection, low-frequency amplification, and filtering, on an MR signal and may transmit the generated signals to the signal transceiver 1120.

Also, the signal controller 1141 may perform a composition process or difference calculation on data obtained from the signal transceiver 1120. The composition process may include an addition process on a pixel and a maximum intensity projection (MIP) process.

The image processor 1142 may process an MR signal that is received from the signal transceiver 1120 and may generate MR image data about the object.

The image processor 1142 may perform various signal processing, such as amplification, frequency transformation, phase detection, low-frequency amplification, and filtering, on the MR signal that is received from the signal transceiver 1120.

The image processor 1142 may arrange digital data in, for example, a k space (which is called a Fourier space or a frequency space) of a memory, and may reconstruct the digital data into image data through 2D or 3D Fourier conversion.

The image processor 1142 may perform a composition process or difference calculation process on image data. The composition process may include an addition process on a pixel and a MIP process. The image processor 1142 may store not only the rearranged image data but also image data on which a composition process or a difference calculation process is performed, in a memory or an external server.

The image processor 1142 may perform various signal processing in parallel. For example, the image processor 1142 may perform signal processing in parallel on a plurality of MR signals that are received by a multi-channel RF coil and may reconstruct the plurality of MR signals into image data.

The interface 150 includes an output interface 1152 and an input interface 1151 that may enable the medical imaging apparatus 1100 to communicate with the user.

The user may input information about the object, a parameter, a scan condition, a pulse sequence, image composition, or difference calculation by using the input interface 1151.

In an exemplary embodiment, the input interface 1151 may receive a user input that selects an ETL from the user. Also, the input interface 1151 that may receive a user input that corrects, adds, or deletes a flip angle schedule.

Examples of the input interface 1151 may include a keyboard, a mouse, a trackball, a voice recognizer, a gesture recognizer, and a touchscreen, and the input interface 1151 may include various input devices within a scope that is obvious to one of ordinary skill in the art.

The output interface 1152 may output image data that is restored or reconstructed by the operator 1140 to the user. Also, the output interface 1152 may output information that is used for the user to operate an MRI system such as a user interface (UI), user information, or object information.

In an exemplary embodiment, the output interface 1152 may divide an MR image that is generated according to an intensity of a signal that is obtained into intervals and may display the intervals.

Examples of the output interface 1152 may include a speaker, a printer, a cathode-ray tube (CRT) display, a liquid-crystal display (LCD), a plasma display panel (PDP) display, an organic light-emitting diode (OLED) display, a field emission display (FED), a light-emitting diode (LED) display, a variable-frequency drive (VFD) display, a digital light processing (DLP) display, a primary flight display (PFD), a 3D display, and a transparent display, and the output interface 1152 may include various output devices within a scope that is obvious to one of ordinary skill in the art.

The communication interface 1160 may transmit and receive data to and from a hospital server or another medical apparatus in a hospital, which is connected through a picture archiving and communication system (PACS), and perform data communication according to the digital imaging and communications in medicine (DICOM) standard.

The communication interface 1160 may be connected to a network by wire or wirelessly to communicate with a server, a medical apparatus, or a portable device.

In detail, the communication interface 1160 may transmit and receive data related to the diagnosis of an object through the network, and may also transmit and receive a medical image captured by the medical apparatus, such as a CT apparatus, an MRI apparatus, or an X-ray apparatus. In addition, the communication interface 1160 may receive a diagnosis history or a treatment schedule of the object from the server and use the same to diagnose the object. The communication interface 1160 may perform data communication not only with the server or the medical apparatus in a hospital, but also with the portable device, such as a mobile phone, a personal digital assistant (PDA), or a laptop of a doctor or patient.

Also, the communication interface 1160 may transmit information about a malfunction of the MRI system or about medical image quality to the user through the network, and receive a feedback regarding the information from the user.

The communication interface 1160 may include at least one component enabling communication with an external apparatus. For example, the communication interface 1160 includes a short-range communication interface 1161, a wired communication interface 1162, and a wireless communication interface 1163.

The short-range communication interface 1161 refers to a module for performing short-range communication with an apparatus within a predetermined distance. Examples of short-range communication technology according to an exemplary embodiment include, but are not limited to, a wireless local area network (LAN), Wi-Fi, Bluetooth, Zig-Bee, Wi-Fi direct (WFD), ultra wideband (UWB), infrared data association (IrDA), Bluetooth low energy (BLE), and near field communication (NFC).

The wired communication interface 1162 refers to a module for performing communication by using an electric signal or an optical signal. Examples of wired communication technology include wired communication techniques using a pair cable, a coaxial cable, and an optical fiber cable, and other well known wired communication techniques.

The wireless communication interface 1163 transmits and receives a wireless signal to and from at least one selected from a base station, an external apparatus, and a server in a mobile communication network. Here, the wireless signal may be a voice call signal, a video call signal, or data in any one of various formats according to transmission and reception of a text/multimedia message.

Although the signal transceiver 1120, the monitor 1130, the operator 1140, the interface unit 1150, and the communication interface 1160 are separate elements in FIG. 11, it will be understood by one of ordinary skill in the art that functions performed by the signal transceiver 1120, the monitor 1130, the operator 1140, the interface 1150, and the communication interface 1160 may be performed by other elements. For example, although the image processor 1142 converts an MR signal that is received by a signal receiver 1123 into a digital signal, the signal receiver 1123 or the RF coil 1113 may directly convert an MR signal into a digital signal. The signal receiver 1123 and the interface 1150 are respectively corresponding to the signal receiver 170 and the interface 180 of FIG. 2.

The gantry 1110, the RF coil 1113, the signal transceiver 1120, the monitor 1130, the operator 1140, the interface 1150, and the communication interface 1160 may be connected to one another in a wired or wireless manner. When the gantry 1110, the RF coil 1113, the signal transceiver 1120, the monitor 1130, the operator 1140, the interface 1150, and the communication interface 1160 are connected to one another in a wireless manner, an apparatus for synchronizing clocks therebetween may be further included. The gantry 1110, the RF coil 1113, the signal transceiver 1120, the monitor 1130, the operator 1140, the interface 1150, and the communication interface 1160 may communicate through various communication methods within a scope that is obvious to one of ordinary skill in the art, for example, high-speed digital interface such as low voltage differential signaling (LVDS), asynchronous serial communication such as universal asynchronous receiver transmitter (UART), synchronous serial communication, a low latency network protocol such as a controller area network (CAN), or optical communication.

While not restricted thereto, an exemplary embodiment can be embodied as computer-readable code on a computer-readable recording medium. For example, a control program that controls the above-described operations may be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units can include circuitry, a processor, a microprocessor, etc., and may execute a computer program stored in a computer-readable medium.

The foregoing exemplary embodiments and advantages are examples and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A medical imaging apparatus comprising:
a signal controller configured to determine flip angles respectively corresponding to radio frequency (RF) refocusing pulses included in a fast spin-echo (FSE) pulse sequence, based on a pseudo-steady state model of a flip angle schedule;
an RF transmitter configured to apply an RF excitation pulse to an object, and apply the RF refocusing pulses to the object based on the determined flip angles; and
an image processor configured to generate a magnetic resonance (MR) image based on an MR signal that is received from the object.

2. The medical imaging apparatus of claim 1, wherein the flip angle schedule is determined based on a target tissue of the object.

3. The medical imaging apparatus of claim 1, wherein the signal controller is configured to:
determine a first echo train (ET) interval and a second ET interval based on a target tissue of the object;
determine a first gradient corresponding to the first ET interval and a second gradient corresponding to the second ET train interval, based on the pseudo-steady state model; and
determine the flip angles respectively corresponding to the RF refocusing pulses, based on the first gradient and the second gradient.

4. The medical imaging apparatus of claim 3, wherein the signal controller is configured to determine flip angles corresponding to a start point and an end point of each of the first ET interval and the second ET interval, based on the flip angle schedule.

5. The medical imaging apparatus of claim 1, wherein a flip angle corresponding to a first RF refocusing pulse, among the RF refocusing pulses, is 180°.

6. The medical imaging apparatus of claim 1, further comprising:
a gradient transmitter configured to apply a diffusion gradient magnetic field to the object before and after a first refocusing pulse, among the RF refocusing pulses, is applied; and
a signal receiver configured to receive an MR signal from the object to which the diffusion gradient magnetic field is applied,
wherein the image processor is configured to generate the MR image based on the received MR signal.

7. The medical imaging apparatus of claim 6, wherein the diffusion gradient magnetic field is generated in gradient magnetic fields in directions of X, Y, and Z axes.

8. The medical imaging apparatus of claim 6, further comprising an output interface configured to:
divide the MR image into intervals according to an intensity of the MR signal; and
display the intervals.

9. The medical imaging apparatus of claim 1, further comprising an input interface configured to receive a user input,
wherein the signal controller is further configured to determine an echo train length of the FSE pulse sequence based on the user input.

10. The medical imaging apparatus of claim 1, further comprising:
a signal receiver configured to receive a magnetic resonance (MR) signal from the object.

11. A method performed by a medical imaging apparatus to generate an image, the method comprising:
determining flip angles respectively corresponding to radio frequency (RF) refocusing pulses included in a fast spin-echo (FSE) pulse sequence, based on a pseudo-steady state model of a flip angle schedule;
applying an RF excitation pulse to an object;
applying the RF refocusing pulses to the object based on the determined flip angles; and
generating a magnetic resonance (MR) image based on an MR signal that is received from the object.

12. The method of claim 11, wherein the flip angle schedule is determined based on a target tissue of the object.

13. The method of claim 11, wherein the determining the flip angles comprises:
determining a first echo train (ET) interval and a second ET interval based on a target tissue of the object;
determining a first gradient corresponding to the first ET interval and a second gradient corresponding to the second ET interval, based on the pseudo-steady state model; and
determining the flip angles respectively corresponding to the RF refocusing pulses, based on the first gradient and the second gradient.

14. The method of claim 13, wherein the determining the first gradient and the second gradient comprises determining flip angles corresponding to a start point and an end point of each of the first ET interval and the second ET interval, based on the flip angle schedule.

15. The method of claim 11, wherein a flip angle corresponding to a first refocusing pulse, among the RF refocusing pulses, is 180°.

16. The method of claim 11, further comprising:
applying a diffusion gradient magnetic field to the object before and after a first RF refocusing pulse, among the RF refocusing pulses, is applied; and
receiving an MR signal from the object to which the diffusion gradient magnetic field is applied,
wherein the generating comprises generating the MR image based on the received MR signal.

17. The method of claim 16, wherein the diffusion gradient magnetic field is generated in gradient magnetic fields in directions of X, Y, and Z axes.

18. The method of claim 16, further comprising:
dividing the MR image into intervals according to an intensity of the MR signal; and
displaying the intervals.

19. The method of claim 11, further comprising:
receiving a user input; and
determining an echo train length of the FSE pulse sequence based on the user input.

20. A non-transitory computer-readable storage medium storing a program comprising instructions configured to cause a computer to:
determine flip angles respectively corresponding to radio frequency (RF) refocusing pulses included in a fast spin-echo (FSE) pulse sequence, based on a pseudo-steady state model of a flip angle schedule;
apply an RF excitation pulse to an object;
apply the RF refocusing pulses to the object based on the determined flip angles; and
generate a magnetic resonance (MR) image based on an MR signal that is received from the object.

* * * * *